(12) United States Patent
Larsson et al.

(10) Patent No.: US 8,008,540 B2
(45) Date of Patent: Aug. 30, 2011

(54) TRANSGENIC NON-HUMAN ANIMAL FOR USE IN RESEARCH MODELS FOR STUDYING PARKINSON'S DISEASE

(75) Inventors: Nils-Göran Larsson, Huddinge (SE); Mats Ekstrand, Huddinge (SE); Lars Olson, Huddinge (SE)

(73) Assignee: Kampavata AB (SE)

( * ) Notice: Subject to any disclaimer, the term of this patent is extended or adjusted under 35 U.S.C. 154(b) by 634 days.

(21) Appl. No.: 11/631,729

(22) PCT Filed: Jul. 7, 2005

(86) PCT No.: PCT/SE2005/001136
§ 371 (c)(1),
(2), (4) Date: Dec. 19, 2007

(87) PCT Pub. No.: WO2006/004552
PCT Pub. Date: Jan. 12, 2006

(65) Prior Publication Data
US 2008/0222738 A1    Sep. 11, 2008

Related U.S. Application Data

(60) Provisional application No. 60/521,813, filed on Jul. 7, 2004.

(51) Int. Cl.
C12N 15/00 (2006.01)
A01K 67/027 (2006.01)
G01N 33/00 (2006.01)
(52) U.S. Cl. .................... 800/25; 800/18; 800/3
(58) Field of Classification Search ............ None
See application file for complete search history.

(56) References Cited

U.S. PATENT DOCUMENTS 4,683,195 A    7/1987  Mullis et al.
2002/0161049 A1  10/2002  Kaddurah-Daouk et al.

FOREIGN PATENT DOCUMENTS

| WO | 9810057 A1 | 3/1998 |
| WO | 9842824 A2 | 10/1998 |
| WO | 0168065 A2 | 9/2001 |
| WO | 0238759 A2 | 5/2002 |

OTHER PUBLICATIONS

Wang et al. Nature Genet. 21:133-137; 1998.*
Clark et al. Nature Reviews: 4: 825-833, 2003.*
Dauer et al. Neuron 39, 889-909, 2003.*
Schapira, Adv Neurol 86, 155-62, 2001.*
Mizuno et al. J Neurochem 48, 1787-93, 1987.*
Betarbet et al. Nat Neurosci 3, 1301-6, 2000.*
International Search Report, PCT/SE2005/001136, dated Oct. 13, 2005.
Nils-Goran Larsson et al, Nature genetics, 18; 231-236 (1998).
C. Graff et al., Journal of Internal Medicine, 246; 11-23 (1999).
M. Flint Beal, Nature Reviews. 2; 325-332 (2001).
Lene Sorensen et al, The Journal of Neuroscience, 21; 8082-8090 (2001).
Dagerlind et al., Histochemistry 98, 39-49. (1992).
Dawson et al., Science 302, 819-22 (2003).
Deumens et al., Exp Neurol 175, 303-17 (2002).
Ekstrand et al., Hum. Mol. Genet. 13, 935-944 (2004).
Falkenberg et al. Nat. Genet. 31, 289-294 (2002).
Fisher et al., J. Biol. Chem. 260, 11330-11338 (1985).
Gu et al., Science 265, 103-106 (1994).
Hansson et al., Proc Natl Acad Sci USA 101, 3136-3141 (2004).
Hokfelt et al., Histochemie 33, 231-54 (1973).
Jenner, P., Oxidative Stress in Parkinson's Disease, Ann. Neurol., 53 Suppl 3, S26-36; Discussion S36-8 (2003).
Langston et al., Science 219, 979-80 (1983).
Larsson et al., Annu. Rev. Genet. 29, 151-178 (1995).
Li et al., Proc. Natl. Acad Sci. USA 97, 3467-72 (2000).
Mizuno, Y. et al., Bioch. Biophys. Res. Comm. 163, 1450-1455 (1989).
Parisi et al., Science 252, 965-969 (1991).
Saraste, Science 283, 1488-93 (1999).
Shimohama et al., Trends Mol Med 9, 360-5 (2003).
Silva et al., Nat. Genet. 26, 336-340 (2000).
Thiruchelvam et al., J Neurosci 20, 9207-14 (2000).
Ungerstedt, Acta Physiol Scand Suppl 367, 69-93 (1971).
van der Walt, et al., Am J Hum Genet 72, 804-11 (2003).
Wredenberg et al., Proc Natl Acad Sci USA 99, 15066-71 (2002).
Zetterstrom et al., Neuroscience 62, 899-918. (1994).
Supplemental European Search Report, EP05756804, dated Jun. 24, 2010.
Ekstrand M. et al., "Manipulating Respiratory Chain Function in the Adult Mouse Fore-Brain"; Abstracts of the Annual Meeting of the Society for Neuroscience, Society for Neuroscience, Washington DC, US vol. 26, No. 1102, Nov. 4, 2000, p. 219.
Donovan, D.M. et al.; "Dopamine transporter: Promoter Characterization and Overexpression in Transgenic Mice", Society for Neuroscience Abstracts, V. 19, No. 1-3, Nov. 7, 1993, p. 745.
Wang et al.; "Increased in Vivo Apoptosis in Cells Lacking Mitochondrial DNA Gene Expression", PNAS V.98, No. 7, Mar. 27, 2001; pp. 4038-4043.
Greenwood, T.A. et al.; "Promoter and Intronic Variants Affect the Transcriptional Regulation of the Human Dopamine Transporter Gene", Genomics, V. 82, No. 5, Nov. 1, 2003, pp. 511-520.
Zhuang, X. et al.; "Targeted Gene Expression in Dopamine and Serotonin Neurons of the Mouse Brain", J. Neurosci. Methods, V. 143, No. 1, Apr. 15, 2005, pp. 27-32.

(Continued)

Primary Examiner — James D. (Doug) Schultz
(74) Attorney, Agent, or Firm — Lerner, David, Littenberg, Krumholz & Mentlik, LLP

(57) ABSTRACT

The invention relates to a transgenic mouse model with deficient respiratory chain function in dopamine (DA) neurons. By suppressing or deleting the mitochondrial transcription factor A (Tfam) in DA neurons, a mouse model is obtained, which reproduces key pathophysiological features of Parkinson's disease (PD), i.e., slow progressive loss of DA terminals in striatum and loss of DA neurons in substantia nigra pars compacta; alpha-synuclein immunoreactivity including intracellular inclusions similar to Lewy bodies in affected areas prior to and during cell loss; progressive movement disorder associated with abnormal gait, tremor and rigid limbs. The mouse model can be used to develop pharmacological, gene therapy or cell therapy treatments for PD.

5 Claims, 5 Drawing Sheets

OTHER PUBLICATIONS

Ekstrand, M. et al.; Progressive Parkinsonism in Mice with Respiratory-Chain-Deficient Dopamine Neurons, PNAS, V. 104, No. 4, Jan. 23, 2007, pp. 1325-1330.

Belin et al.; "Association Study of Two Genetic Variants in Mitochondrial Transcription Factor A (TFAM) in Alzheimer's and Parkinson's Disease", Neurosci. Letters, V. 420, No. 3, Jun. 4, 2007, pp. 257-262.

Alvarez et al.; "Mitochrondrial transcription factor A (TFAM) Gene Variation in Parkinson's Disease", Neurosci. Letters, V. 432, No. 1, Dec. 15, 2007, pp. 79-82.

Ekstrand M.I. et al.; "The MitoPark Mouse: an Animal Model of Parkinson's Disease with Impaired Respiratory Chain Function in Dopamine Neurons", Parkinsonism and Related Disorders, V. 15, Dec. 1, 2009, pp. S185-S188.

Gaweda-Walerych, K. et al.; "Mitochondrial Transcription Factor A Variants and the Risk of Parkinson's disease", Neurosci. Letters, V. 469 No. 1, Jan. 18, 2010, pp. 24-29.

* cited by examiner

TRANSGENIC NON-HUMAN ANIMAL FOR USE IN RESEARCH MODELS FOR STUDYING PARKINSON'S DISEASE

SEQUENCE LISTING

The instant application contains a Sequence Listing, and one compact disc (CD) containing the computer readable form (CRF) of this Sequence Listing was submitted to the USPTO on May 2, 2008. The material contained on this CD is hereby incorporated by reference in its entirety. Said CRF was created in April of 2008 and contains the ASCII file, "p002687us seq listing 080417 ST25.txt" which is 4.00 KB in size.

FIELD OF THE INVENTION

The invention relates to research models for studying disease. Specifically, the invention relates to research models for studying Parkinson's disease. Even more specifically, the invention relates to a transgenic non-human animal, in particular a mouse, that can be used as a model system when studying Parkinson's disease. The invention also provides screening methods aiming at finding and identifying pharmaceuticals, therapies and treatments for Parkinson's disease.

BACKGROUND AND SUMMARY OF THE INVENTION

Cardinal symptoms in Parkinson's disease (PD) result primarily from death of dopaminergic (DA) neurons in substantia nigra pars compacta (SNpc) (Dauer et al., *Neuron* 39, 889-909 (2003); Dawson et al., *Science* 302, 819-22 (2003)). Current interventions ameliorate symptoms but there is no treatment to halt or delay loss of DA neurons. Several lines of evidence suggest that respiratory chain dysfunction is involved in the pathogenesis of PD (Dauer et al., *Neuron* 39, 889-909 (2003); Dawson et al., *Science* 302, 819-22 (2003)): (1) A deficient function of the respiratory chain has been reported in cell lines and tissues from PD patients (Mizuno, Y. et al., *Bioch. Biophys. Res. Comm.* 163, 1450-1455 (1989); Schapira, *Adv Neurol* 86, 155-62 (2001)). (2) Certain mitochondrial DNA (mtDNA) polymorphisms reduce the risk of PD (van der Walt, et al., *Am J Hum Genet* 72, 804-11 (2003)). (3) The toxin MPP+ inhibits complex I of the respiratory chain and it causes parkinsonism after selective uptake in DA neurons (Langston et al., *Science* 219, 979-80 (1983); Mizuno et al., *J Neurochem* 48, 1787-93 (1987)). (4) The pesticide rotenone is a strong inhibitor of complex I and long term exposure causes parkinsonism in rats (Betarbet et al., *Nat Neurosci* 3, 1301-6 (2000)). (5) The herbicide paraquat inhibits complex I and can in combination with other agents cause selective degeneration of DA neurons (Thiruchelvam et al., *J Neurosci* 20, 9207-14 (2000)). In addition, the mitochondrial respiratory chain is a major producer of ROS and oxidative stress is directly involved in the cascade of biochemical changes causing DA cell death (Thiruchelvam et al., *J Neurosci* 20, 9207-14 (2000)).

The respiratory chain consists of five enzyme complexes formed by ~100 different protein subunits that perform the process of oxidative phosphorylation to generate adenosine triphosphate (ATP), which is used as the energy source for a large number of cellular processes (Saraste, *Science* 283, 1488-93 (1999)). The biogenesis of the respiratory chain is unique in its bipartite dependence on both nuclear and mtDNA genes. The expression and maintenance of mtDNA is completely controlled by nuclear genes, as exemplified by mitochondrial transcription factor A (TFAM) which regulates mtDNA transcription (Fisher et al., *J. Biol. Chem.* 260, 11330-11338 (1985); Parisi et al., *Science* 252, 965-969 (1991); Larsson et al., *Annu. Rev. Genet.* 29, 151-178 (1995); Falkenberg et al. *Nat. Genet.* 31, 289-294 (2002)) and mtDNA copy number (Ekstrand et al., *Hum. Mol. Genet.* 13, 935-944 (2004)). We have constructed a conditional knockout allele (Gu et al., *Science* 265, 103-106 (1994)) by inserting loxP sequences into the Tfam locus to generate Tfam$^{loxP}$ animals (Larsson et al., *Nat. Genet.* 18, 231-6 (1998)). The Tfam$^{loxP}$ mice have normal TFAM protein expression and normal oxidative phosphorylation capacity (Wang et al., *Nat. Genet.* 21, 133-7 (1999)). The protein cre recombinase will specifically recognize and recombine loxP sequences, thereby deleting any DNA between them. By controlling the expression of cre we can in our system choose in what tissue or cell type we want to knock out Tfam. We have extensively documented that this system allows very efficient germ line and tissue-specific knockout of Tfam (Larsson et al., *Nat. Genet.* 18, 231-6 (1998); Wang et al., *Nat. Genet.* 21, 133-7 (1999); Li et al., *Proc. Natl. Acad. Sci. USA* 97, 3467-72 (2000); Hansson et al., *Proc Natl Acad Sci USA* 101, 3136-3141 (2004); Silva et al., *Nat. Genet.* 26, 336-340 (2000); Sorensen et al., *J. Neurosci.* 21, 8082-8090 (2001); Wredenberg et al., *Proc Natl Acad Sci USA* 99, 15066-71 (2002)). Heterozygous germ line knockout animals (+/Tfam$^-$) have a reduction of mtDNA copy number in all tissues and a moderate respiratory chain deficiency in the heart, whereas homozygous germ line knockouts (Tfam$^-$/Tfam$^-$) die in mid-gestation due to lack of mtDNA and absence of oxidative phosphorylation (Larsson et al., *Nat. Genet.* 18, 231-6 (1998)). We have also studied pathophysiological events associated with mitochondrial dysfunction by selectively disrupting Tfam in heart muscle cells (Wang et al., *Nat. Genet.* 21, 133-7 (1999); Li et al., *Proc. Natl. Acad Sci. USA* 97, 3467-72 (2000); Hansson et al., *Proc Natl Acad Sci USA* 101, 3136-3141 (2004)), insulin-secreting β-cells (Silva et al., *Nat. Genet.* 26, 336-340 (2000)), forebrain neurons (Sorensen et al., *J. Neurosci.* 21, 8082-8090 (2001)) and skeletal muscle cells (Wredenberg et al., *Proc Natl Acad Sci USA* 99, 15066-71 (2002)).

A critical gap in our knowledge of PD is a validated and widely acceptable rodent model in which endogenous disruption of respiratory enzymes leads to a PD-like phenotype. An ideal genetic model for PD would have the following characteristics (Beal, *Nat Rev Neurosci* 2, 325-34 (2001)): (1) Normal number of DA neurons at birth with a gradual loss during adulthood. (2) Easily detectable motor deficits including bradykinesia, rigidity and resting tremor. (3) Histology showing typical α-synuclein pathology including formation of the intracellular inclusions known as Lewy bodies. (4) Robust genetics allowing easy propagation of the genotype. (5) A progressive disease course of just a few months for rapid testing of different therapeutic strategies.

Almost all available in vivo models of PD are based on the administration of neurotoxins to animals. The first agent used to produce an animal model of PD was 6-OHDA (Ungerstedt, *Acta Physiol Scand Suppl* 367, 69-93 (1971)). This toxin is normally injected unilaterally directly into the substantia nigra, the medial forebrain bundle or the striatum causing a selective loss of DA neurons. 6-OHDA lesions do not result in typical Lewy body formation and can cause nonspecific damage to other neurons. When injected into the substantia nigra 6-OHDA treatment is acute, causing a rapid cell loss not resembling the progressive nature of PD. If injected into striatum the effect is slower (<4 weeks) but then only partial. This limits researchers to study only the end-stage or a very short progression of the disease (Beal et al., *Nat Rev Neurosci* 2, 325-34 (2001); Ungerstedt, *Acta Physiol Scand Suppl* 367, 69-93 (1971); Deumens et al., *Exp Neurol* 175, 303-17 (2002)).

The most widely used animal model of PD today is acute systemic administration of MPTP which in primates causes parkinsonism with a selective loss of DA neurons in the substantia nigra. Rodents are much less sensitive to MPTP and require a higher dose while the typical behavioral symptoms of parkinsonism rarely appear. The main disadvantages of MPTP is the resistance of most rodents and the acute nature of the model preventing researchers from studying the progression of the disease (Shimohama et al., *Trends Mol Med* 9, 360-5 (2003)).

Recently it was discovered that systemic treatment with low doses of the naturally occurring pesticide rotenone over time causes parkinsonism in rats. Treated animals show a selective loss of DA neurons in the substantia nigra associated with intracellular inclusions similar to Lewy bodies. The outcome of rotenone treatment is highly variable as only a part of the treated rats develop PD-like pathology and some strains do not respond at all to the drug (Betarbet et al., *Nat Neurosci* 3, 1301-6 (2000)). All these pharmacological models also suffer from the inherent risk of other pleiotropic effects of systemic drug administration.

In the present document we describe the generation of a mouse with a specific disruption of Tfam and hence oxidative phosphorylation in DA neurons only. We use the dopamine transporter (DAT) locus to direct the expression of cre recombinase to this specific cell type. Such mice over the time of several months develop a PD-like behavioral phenotype associated with loss of DA neurons in the SNpc and pathology typical for the disease. The generated animal model faithfully reproduces key pathophysiological features of PD, i.e. slow progressive loss of DA terminals in striatum and loss of DA neurons in SNpc; α-synuclein reactivity including intracellular inclusions similar to Lewy bodies in affected areas prior to and during cell loss; progressive movement disorder, that is partially reversed by L-DOPA treatment, associated with abnormal gait, tremor and rigid limbs. This model will be a valuable tool for testing pharmacological, gene and cell therapies to counteract or cure PD.

As used herein, the term "genetically modified" refers to any purposeful alteration of the naturally-occurring genome of an animal. For example, sequences can be inserted into the genome which, when activated, can cause selective deactivation of a particular gene adjacent to the inserted sequence.

The term "dysfunction" refers to any deviation from normal or naturally-occurring function in a disease-free state.

The term "naturally exhibiting" refers to the characteristics or traits occurring under normal environmental and physiological conditions.

As used herein, the term "Tfam" relates to mitochondrial transcription factor A (Fisher et al., *J. Biol. Chem.* 260, 11330-11338 (1985); Parisi et al., *Science* 252, 965-969 (1991); Larsson et al., *Annu. Rev. Genet.* 29, 151-178 (1995); Falkenberg et al. *Nat. Genet.* 31, 289-294 (2002)) and mtDNA copy number (Ekstrand et al., *Hum. Mol. Genet.* 13, 935-944 (2004)).

As disclosed herein, the terms "Parkinson mouse" and "homozygous knockout animals" both relate to transgenic mice comprising the 5' end of the dopamine transporter gene fused to a DNA sequence encoding cre recombinase as well as a DNA sequence comprising a sequence encoding Tfam which sequence also contains LoxP sequences (+/DAT-cre; $Tfam^{loxP}/Tfam^{loxP}$). This recombination leads to cell type specific homozygous disruption of Tfam and hence oxidative phosphorylation in DA neurons only, and accordingly such mice display symptoms of Parkinson's disease.

SUMMARY OF THE INVENTION

In a first aspect, the present invention relates to a transgenic non-human mammal genetically modified to have respiratory chain dysfunction or genetically modified to lack respiratory chain function in dopaminergic (DA) neurons only. In a preferred embodiment, said mammal is a rodent, preferably a rat or a mouse.

Furthermore, it is preferred that said animal is genetically modified to lack oxidative phosphorylation function in dopaminergic (DA) neurons only, or to have oxidative phosphorylation dysfunction in dopaminergic (DA) neurons only. This can be done by selectively suppressing or deleting mitochondrial transcription factor A (Tfam) in dopaminergic (DA) neurons In a second aspect, the present invention provides a method for producing a transgenic non-human animal comprising the steps of:

a) providing a first group of non-human animals, said first group of non-human animals being homozygous for a loxP-flanked Tfam allele ($Tfam^{loxP}/Tfam^{loxP}$);
b) providing a targeting vector comprising a NLS-cre gene inserted into the dopamine transporter locus;
c) introducing said targeting vector into embryonic stem cells originating from said non-human animal by homologous recombination;
d) growing said recombinant embryonic stem cells according to known methods thereby obtaining a transgenic non-human animal expressing cre in dopaminergic (DA) neurons;
e) crossing said first group of non-human animals being homozygous for a loxP-flanked Tfam allele ($Tfam^{loxP}/Tfam^{loxP}$) with said non-human animal expressing cre in dopaminergic (DA) neurons, thereby obtaining a transgenic non-human mammal genetically modified to have respiratory chain dysfunction or genetically modified to lack respiratory chain function in dopaminergic (DA) neurons only.

In a third aspect, the present invention relates to a method for investigating whether a chemical compound could be used for treating Parkinson's disease, comprising the steps of a) providing a transgenic non-human animal according to anyone of claims 1-4;
b) providing a chemical compound to be tested;
c) exposing said transgenic non-human animal to said compound to be tested;
d) controlling whether said chemical compound to be tested affects locomotion and/or rearing of the transgenic non-human animals, which indicates that said compound could be used for treating Parkinson's disease.

"Amino acid sequence", "polypeptide sequence" and "peptide sequence" are used interchangeably herein to refer to a sequence of amino acids.

"Nucleic acid molecule", "nucleic acid sequence", "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20-25 nucleotides, which can be used as a probe or amplimer.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

Vectors are frequently used in the experiments disclosed in the present application. A suitable vector can be a plasmid, cosmid, phage, etc. Vectors are standard tools of molecular biologists (J. Sambrook et al. (1989) Molecular Cloning: A Laboratory Manual, Cold Spring Harbor Press, NY, US, pp 9.31-9.58).

A "selection marker" as used herein refers to a nucleic acid sequence which is used for facilitating screening of successful transformants. Examples of selection markers are antibiotic resistance genes, enzyme genes, etc. Selection markers are standard tools of molecular biologists (J. Sambrook et al. (1989) Molecular Cloning: A Laboratory Manual, Cold Spring Harbor Press, NY, US).

A "transgenic animal" as used herein refers to an animal that includes a transgene which is inserted into a cell and which becomes integrated into the genome either of somatic and/or germ line cells of the. A "transgene" means a DNA sequence which is partly or entirely heterologous (i.e., not present in nature) to the animal in which it is found, or which is homologous to an endogenous sequence (i.e., a sequence that is found in the animal in nature) and is inserted into the animal's genome at a location which differs from that of the naturally occurring sequence. Transgenic animals which include one or more transgenes are within the scope of this invention.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e. particle bombardment) and the like.

The term "compound" refers to any chemical entity, pharmaceutical, drug, and the like that is suspected of having a positive impact on Parkinson's disease. Compounds comprise both known and potential therapeutic compounds. A compound can be considered to positively affect Parkinson's disease if it can be shown that locomotion and rearing of the transgenic non-human mammal increases after exposure to said compound in accordance with behavioral analysis as outlined below.

A compound is said to be "in a form suitable for administration such that the compound is bio-available in the blood of the animal" when the compound may be administered to an animal by any desired route (e.g., oral, intravenous, subcutaneous, intrathecal, intraperitoneal, intramuscular, etc.) and the compound or its active metabolites appears in the blood of the animal in an active form.

Following initial screening, a compound that appears promising is further evaluated by administering various concentrations of the compound to the transgenic animals provided herein in order to determine an approximate therapeutic dosing range.

Animal testing may be supplemented and confirmed by testing on human subjects. However, the animal models herein provided allow the testing of a large number of compounds, both by the methods described above and other methods known in the art, in a system similar in many important respects to that in humans.

"Amplification" is defined as the production of additional copies of a nucleic acid sequence and is generally carried out using polymerase chain reaction technologies well known in the art (Dieffenbach C W and G S Dveksler (1995) PCR Primer, a Laboratory Manual, Cold Spring Harbor Press, Plainview N.Y.). As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule", so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) Molecular Cloning: A Laboratory Manual, Cold Spring Harbor Press, NY, pp 9.31-9.58).

A. A cassette containing an NLS-cre (cre) gene followed by an FRT-flanked neomycin (neo) gene was inserted in the FspI site just upstream of Exon 2. The Intron 1/Exon 2 border was recreated by introducing a short oligo 5' to the NLS-cre gene. Homologous recombination in ES-cells generated the DAT-cre$^{neo}$ locus. The neo gene was later removed by breeding to FLPe deleter mice. B. Southern blot genotyping of BamHI digested genomic DNA. The hybridization probe located outside the area of homology gives bands of different sizes for each of the three DAT loci. C. Routine PCR genotyping of genomic tail DNA. Unspecific recombination of the Tfam locus in tail DNA is not detectable when the neo gene has been removed from the knockin locus. The Tfam locus was genotyped using a three primer protocol that gives specific bands for the wild-type (wt; 404 bp), loxP-flanked (Tfam$^{loxP}$; 437 bp) and knockout (Tfam$^{KO}$; 329 bp) Tfam loci. The presence of either cre knockin loci (DAT-cre$^{neo}$ or DAT-cre) was demonstrated by using PCR primers specific for the cre gene (371 bp). PCR primers spanning the neo gene were used to discriminate between the DAT-cre$^{neo}$ and DAT-cre loci. These primers only give a product in the absence of neo.

Figure 2:
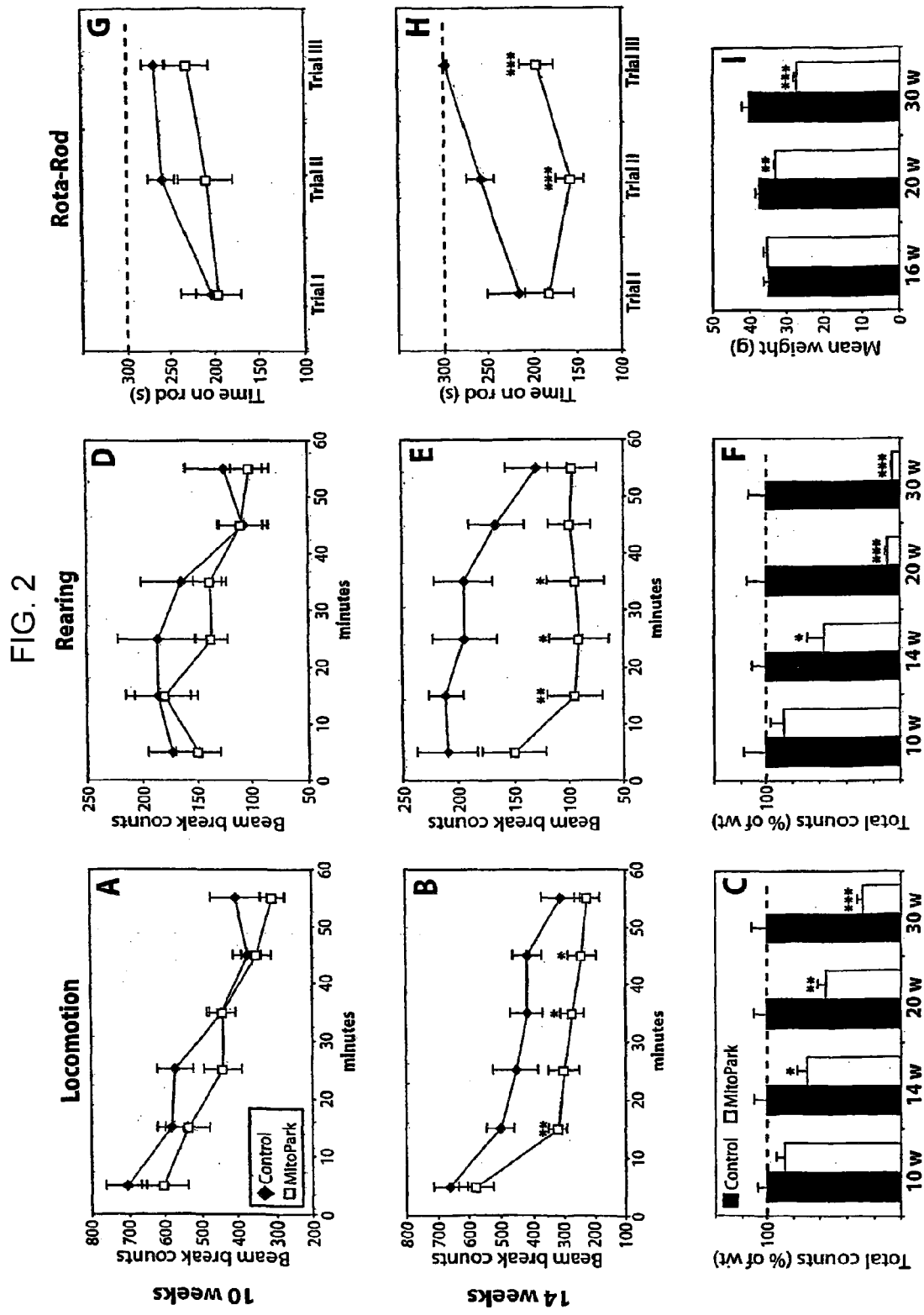

FIG. 2: Analyses of spontaneous activity and motor function:

The locomotion (A-C) and rearing (D-F) activities of homozygous knockout and control mice were measured for 60 minutes in open-field activity cages. The 10 week old homozygous knockout mice did not behave significantly different from age-matched controls (A and D) while 14 week old homozygous knockout mice displayed decreased activity (B and E). Total locomotion (C) and rearing (F) during 60 minutes decreased further in aging homozygous knockout mice, as compared to age-matched controls. G-H. Rota-Rod was used to assess motor function in homozygous knockout mice. 10 week old homozygous knockout mice did not perform significantly different from controls (G) while 14 week old mice performed significantly different from control mice during the second and third trials (H). I. Mean weight of male homozygous knockout and control mice at 16, 20 and 30 weeks of age. Error bars are indicated as ±S.E.M. Statistically significant differences to age-matched controls are indicated as: *$p<0.05$; $p<0.01$; *$p<0.001$.

Figure 3:
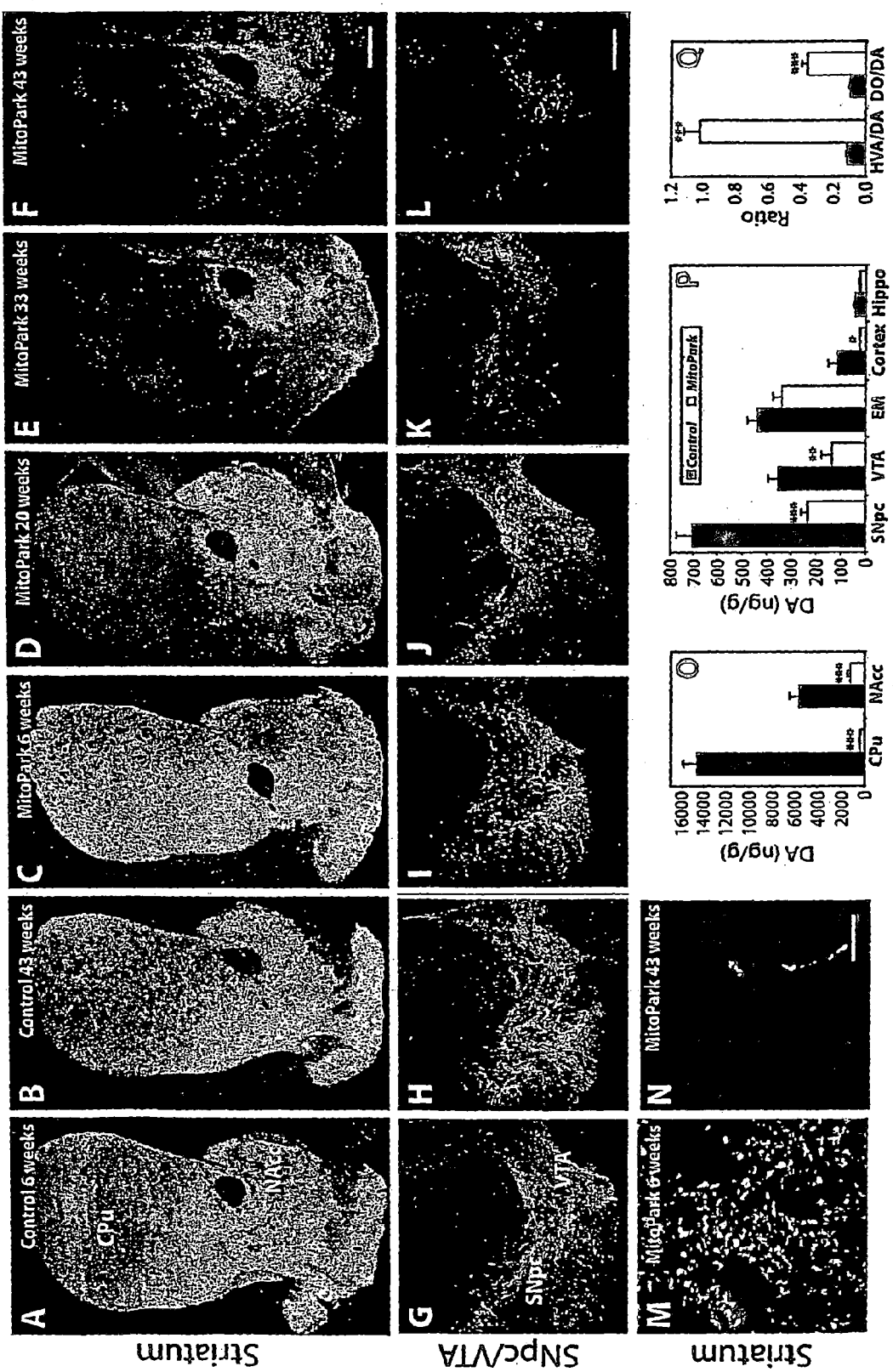

FIG. 3: Histochemical and biochemical analyses of the midbrain DA system.

A-F. TH immunoreactivity in striatum of control (A-B) and homozygous knockout (C-F) mice. Loss of DA terminals starts in dorsolateral caudate putamen (CPu) and progress to affect also more medial and ventral areas of striatum (D-F). In old (43 weeks) homozygous knockout mice only part of nucleus accumbens (NAcc) contain TH immunoreactive fibers (F). Bar=500 µm. G-L. TH immunoreactivity in substantia nigra pars compacta (SNpc) and the ventral tegmental area (VTA) of control (G-H) and homozygous knockout (I-L) mice. Loss of DA neurons is first seen in SNpc but then progresses to involve also VTA (J-L). Bar=400 µm. M-N. High magnification of TH immunoreactive nerve terminals in striatum of 6 and 43 week old homozygous knockout mice. Bar=10 µm. O-P. HPLC measurements of DA levels in striatum (O) as well as other brain regions (P) of 20 week old control and homozygous knockout mice. Q. DA levels related to the DA metabolites HVA or DOPAC as an estimation of DA turnover in striatum of 20 week old control and homozygous knockout mice. Error bars are indicated as ±S.E.M. Statistically significant differences to age-matched controls are indicated as: *$p<0.05$; $p<0.01$; *$p<0.001$.

Figure 4:
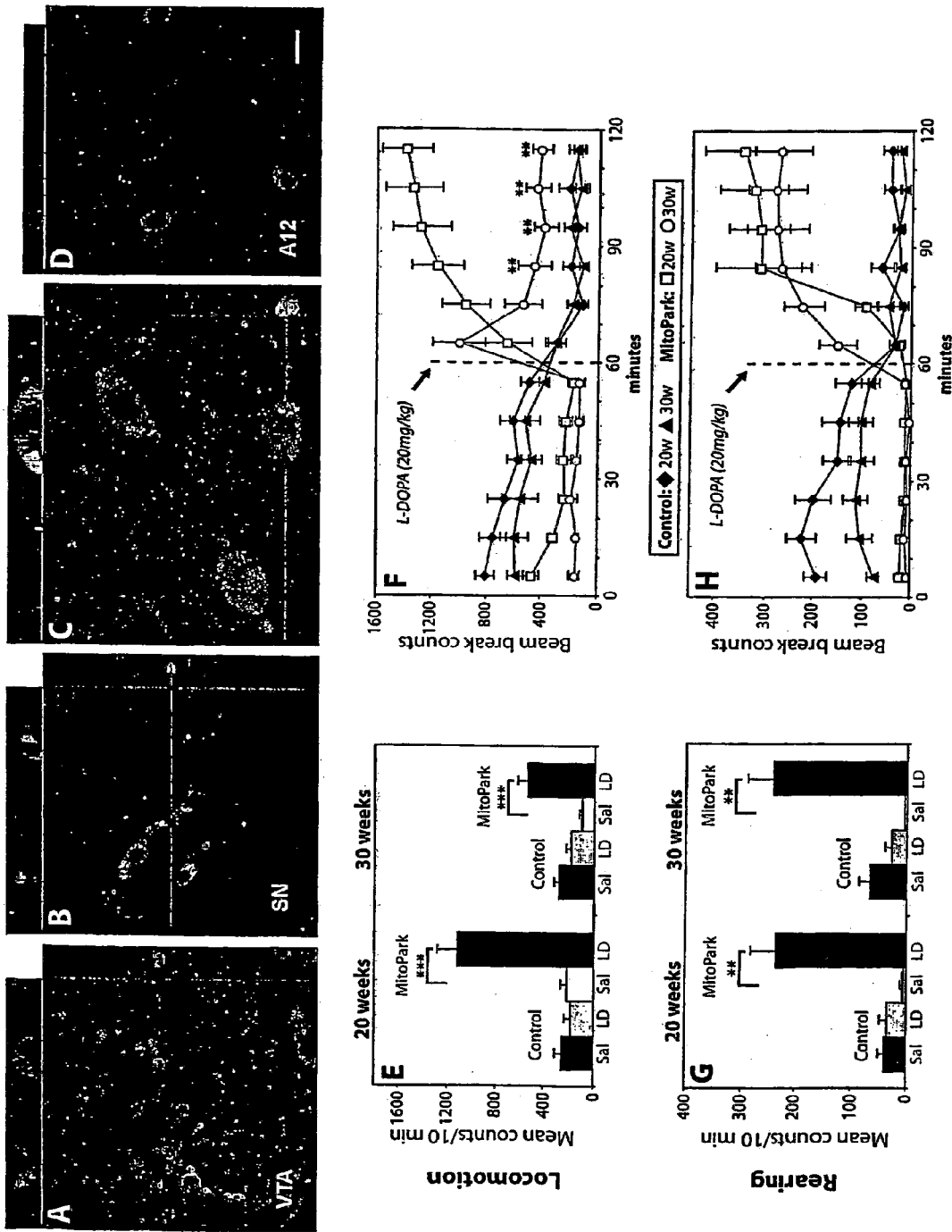

FIG. 4; Formation of intra-cytoplasmic inclusions and L-DOPA treatment.

A and B. Confocal microscopic demonstration of α-synuclein immunoreactive inclusions (green) in TH immunoreactive DA neurons (red) of the ventral tegmental area (VTA) and substantia nigra (SN). C. Example of triple co-localization of TH immunoreactivity (blue), α-synuclein immunoreactivity (green) and ubiquitin immunoreactivity (red) in a midbrain DA neuron of a homozygous knockout mouse. The neuropil of homozygous knockout and control mice contain finely dispersed ubiquitin immunoreactivity. In addition, larger ubiquitin immunoreactive aggregates that also are α-synuclein immunoreactive can be found in the affected DA neurons of homozygous knockout mice. This is seen projected in three planes in the lower right of the three TH immunoreactive neurons (yellow spot). D. Small somata of the tubero-infundibular dopamine system (A12) are TH immunoreactive and do not show any obvious neuropathological changes in 43 weeks old homozygous knockout mice (scale bar: 25 µm). E-H. Cohorts of 20 and 30 week old homozygous knockout or control mice were treated with L-DOPA (20 mg/kg) or saline. Homozygous knockout mice of both ages responded to L-DOPA treatment with increased locomotion (E) and rearing (G). L-DOPA treatment of younger homozygous knockout mice resulted in a greater locomotion response than treatment of older homozygous knockout mice (E-F). The increase of rearing after L-DOPA treatment of homozygous knockout mice was similar in both age groups (G-H). Error bars are indicated as ±S.E.M. The bars show mean locomotion (E) and mean rearing (G) in control and homozygous knockout mice treated with saline (sal) or L-DOPA (LD). Statistically significant differences are indicated with stars: *$p<0.05$; $p<0.01$; *$p<0.001$.

Figure 5:
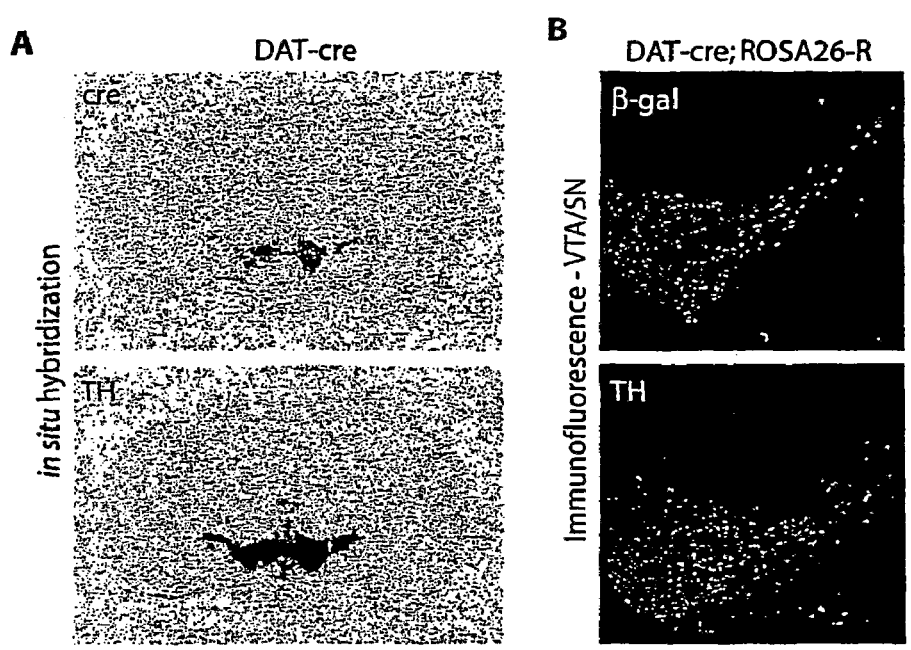

FIG. 5: Dopamine neuron specific expression of cre transgene

A. In situ hybridization of midbrain dopamine neurons. Tyrosine hydroxylase (TH) and cre recombinase specific $^{33}$P-labeled hybridization probes were used to estimate the specificity of cre expression. B. LacZ reporter mice visualization of cre expression. Mice carrying the DAT-cre knockin locus were mated to ROSA26-R reporter mice. Offspring heterozygous for both loci were identified and studied with immunohistochemistry. TH and β-galactosidase (β-gal) specific polyclonal antibodies were used to visualize these proteins in brain sections.

DETAILED DESCRIPTION OF THE INVENTION

Materials and Methods

Generation of DAT-cre Mice

In order to obtain mouse genomic DNA clones containing the 5' end of the dopamine transporter gene (DAT; Solute carrier family 6, member 3) we screened a 129/SvJ λ Fix II phage library (Stratagene) using an 814 bp probe spanning from the promoter region over exon 1 and into intron 1. The probe was generated by PCR using mouse genomic DNA with the forward primer 5'-CAG GGT CGG AGA GTC ATA CAA C-3' (SEQ ID NO 10) and the reverse primer 5'-ATG AAC CAG GTC TTG AGT CTG G-3' (SEQ ID NO 11). Five overlapping clones containing part of the DAT gene were identified and isolated. Restriction enzyme digestion followed by Southern blotting and hybridization with oligo probes was used to make an approximate contig of the five clones. Clone 1, spanning from ~3.7 kb upstream of exon 1 and downstream into intron 5, was released with NotI and subcloned into pBlueScript II SK, generating pME1.

An NLS-cre/FRT-neo-FRT cassette was constructed by subcloning the needed elements in several steps. First the MCS of a pBlueScript II SK was released with SalI-KpnI and replaced with a synthetic oligo containing the necessary cloning sites, inactivating the 3' KpnI site (SacI/PacI/SalI/EcoRI/KpnI/FRT-sequence/XhoI/EcoRI/SacII/AscI/KpnI*), generating pME2. An NLS-cre fragment was released from pML78 (Mark B. Lewandoski, National Cancer Institute at Frederick) using SalI-KpnI and ligated into pME2, generating pME3. Next, a synthetic oligo containing an FRT-sequence was introduced after the polyA in pMC1neo-polyA (provided by Thomas Perlmann, Karolinska Institute), using BamHI and SacII. This neo-FRT construct was then released with XhoI-SacII and ligated into pME3, generating pME4 which was sequenced from both directions.

For final assembly of the targeting construct a new plasmid was generated by replacing the MCS of pBlueScript II SK with an oligo containing restriction sites for the insertion of 5' and 3' homology arms as well as for the NLS-cre/FRT-neo-FRT cassette (SacI/NotI/BamHI/SmaI/PacI/BamHI/AscI/EcoRV/BamHI/EcoRI/KpnI), generating pME5. The 5' and 3' homology arms were released from pME1 with NotI-FspI and FspI-EcoRI, respectively, and inserted into pME5 using NotI-SmaI and EcoRV-EcoRI. The cassette from pME4 was released and inserted between the homology arms using PacI-AscI. The endogenous DAT translational start site is located in exon 2 and since this design actually puts the cassette in intron 1 just before exon 2 we finally introduced a short synthetic oligo recreating the intron 1/exon 2 border at the PacI site just upstream of the cre gene, generating pME6. The insertion site was sequenced to verify the correct integration and direction of the oligo.

The targeting vector was linearized with NotI and electroporated into RI embryonic stem (ES) cells. Candidate recombinant clones were selected for by growth in the presence of G418. Southern hybridization showed a ~30% targeting efficiency of the DAT-locus with the knockin construct. Three correctly targeted clones were injected into C57BL/6J blastocysts which were then implanted into pseudopregnant females. Two of the clones generated medium- to high-grade male chimeras that gave rise to agouti pups when bred to C57BL/6J females, indicating germline transmission of the ES-cell genome containing the targeted DAT-locus. Agouti pups were genotyped using Southern blot as well as PCR.

To remove the FRT-flanked neo gene downstream of the cre gene, mice heterozygous for the targeted DAT-locus (+/DAT-cre$^{neo}$) were mated to FLPe deleter mice, expressing FLPe from a human β-actin promoter. Offspring lacking the neo gene (+/DAT-cre) were identified with Southern blot analysis and kept on a C57BL/6J background.

Generating Parkinson Mice

DAT-cre mice were mated to mice homozygous for a loxP-flanked mitochondrial transcription factor A (Tfam) allele (Tfam$^{loxP}$/Tfam$^{loxP}$) and offspring carrying the DAT-cre locus (+/DAT-cre; +/Tfam$^{loxP}$) were identified with PCR. In a second step such mice were again mated to Tfam$^{loxP}$/Tfam$^{loxP}$ mice to generate homozygous knockout animals (+/DAT-cre; Tfam$^{loxP}$/Tfam$^{loxP}$) and controls (+/Tfam$^{loxP}$ or Tfam$^{loxP}$/Tfam$^{loxP}$).

Southern Blot and PCR Genotyping

For Southern blot analysis, ~10 μg of genomic tail DNA was digested with BamHI, electrophoresed through a 0.8% agarose gel and transferred to a Hybond C+membrane (Amersham). Membranes were hybridized with a 3' probe labeled with [α-$^{32}$P]dCTP (3000 Ci/mmol; Amersham), and visualized by autoradiography using standard procedures.

Routine PCR genotyping for the presence of cre was performed with the forward primer 5'-CAC GAC CAA GTG ACA GCA AT-3' (SEQ ID NO 1) and the reverse primer 5'-AGA GAC GGA AAT CCA TCG CT-3' (SEQ ID NO 2), giving a product of 371 bp in the presence of cre. PCR genotyping to verify that the neo gene is excised by FLPe recombination was done with the forward primer 5'-CCC AAC TTG AGA TGT ATG AA-3' (SEQ ID NO 3) and the reverse primer 5'-CAA GAA GCG CTT TAC TGA C-3' (SEQ ID NO 4), giving a product of 954 bp after excision.

The Tfam locus was genotyped with PCR using a three primer strategy (mt31: 5'-CTG CCT TCC TCT AGC CCG GG-3' (SEQ ID NO 5); mt12: 5'-GTA ACA GCA GAC AAC TTG TG-3' (SEQ ID NO 6); mt36: 5'-CTC TGA AGC ACA TGG TCA AT-3') (SEQ ID NO 12), generating 437, 404 and 329 bp products for Tfam$^{loxP}$, Tfam$^{wt}$ and Tfam$^{KO}$, respectively (Larsson et al., *Nat. Genet.* 18, 231-6 (1998)).

In Situ Hybridization

Probes against the transcripts for tyrosine hydroxylase (5'-GGT GTG CAG CTC ATC CTG GAC CCC CTC CAA GGA GCG CT-3') (SEQ ID NO 7) and cre recombinase (5'-GCC CGG ACC GAC GAT GAA GCA TGT TTA GCT GGC CCA AAT GTT GCT GGA-3'(SEQ ID NO 8) or 5'-CAC CAG AGA CGG AAA TCC ATC GCT CGA CCA GTT TAG TTA CCC CCA GGC-3') (SEQ ID NO 9) were 3'-end labeled with $^{33}$P and used to detect mtRNA in 14 μm cryostat sections from fresh frozen brains by in situ hybridization (Dagerlind et al., *Histochemistry* 98, 39-49. (1992)). A random oligonucleotide probe was used as a negative control. Hybridizations were performed at 42° C. for 16-18 hr, and sections were rinsed five times in 1×SSC, dehydrated, and exposed to photographic emulsion (Kodak NTB2; Eastman Kodak).

Histology and Immunohistochemistry

Mice were perfused with $Ca^{2+}$-free Tyrode's solution, followed by 4% paraformaldehyde with 0.4% picric acid in 0.16 M phosphate buffer. The brains were dissected out, postfixed, and equilibrated to 10% sucrose containing 0.1% sodium azide. Primary antibodies used for indirect immunohistochemistry (Hökfelt et al., *Histochemie* 33, 231-54 (1973); Zetterström et al., *Neuroscience* 62, 899-918. (1994)) included polyclonal antibodies against tyrosine hydroxylase (TH) (1:400; Pel-Freez), β-galactosidase (1:500; Chemicon), glial fibrillary acidic protein 19 (GFAP-19) (1:500; Sigma) and α-synuclein (1:50; Biogenesis). Cryostat sections (14 μm) were incubated with primary antibodies overnight at 4° C., rinsed, and incubated with appropriate FITC- or Cy2-labeled secondary antibodies. Controls included omitting the primary antibody. Sections were analyzed by fluorescence microscopy.

For terminal deoxynucleotidyl transferase-mediated biotinylated UTP nick end (TUNEL) labeling we used the In situ Cell Death Detection (POD) kit (Roche) according to the instructions of the manufacturer.

Behavioral Analyses of Animals

Open field activity was examined in automated activity cages. This consisted of Plexiglas boxes (35×35×18 cm) with a lower and a higher row of infrared sensitive photocells and a microcomputer registering interruption of photocell beams. Animals were tested during the light phase of the light-dark cycle, between 9:00 and 13:00 h. Locomotor activity was registered when animals interrupted the lower row of photocells and rearing was registered when the higher row was interrupted. Animals were individually placed gently in the open field arena and remained there during 60 min. Locomotion and rearing counts were registered every 10 min. For the L-DOPA treatment, spontaneous locomotion and rearing were measured in activity cages as above. Animals were then given i.p. injections of L-DOPA combined with the peripheral dopa decarboxylase inhibitor benzerazide (Madopark 20 mg/kg in PBS; Roche) or PBS and were then immediately put back into the activity cages for another 60 minutes of recording. The scoring of counts was given as mean+/−SEM. Statistical significance was tested using 2-way ANOVA analysis. The open field box was cleaned with 70% alcohol after each test.

Locomotor skill and balance were tested using a rotating rod (Rota-Rod). The mice were given a short practice run in the morning and then three trials were done in the afternoon with one hour between every trial. The speed of the rod increased from 4-40 rpm and each trial was terminated after 300 seconds.

Results

Generation and Breeding of DAT-cre Mice

Figure 1:
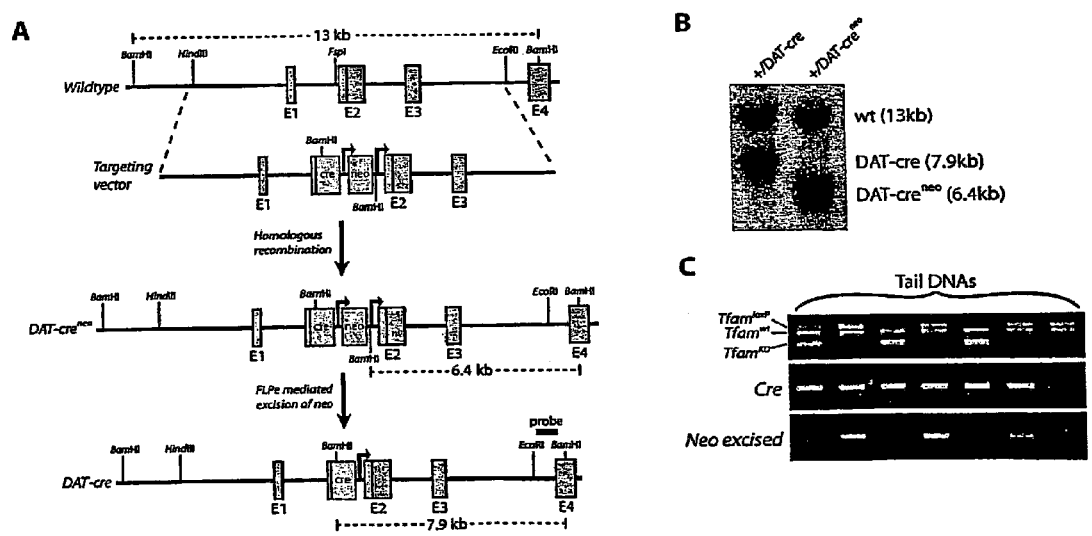
FIG. 1: Knock-in construct and genotyping.

Mice with a cell-type specific expression of cre recombinase in dopaminergic (DA) neurons were generated by knocking in cre at the dopamine transporter locus (DAT; Solute carrier family 6, member 3). A targeting vector was constructed spanning 5.5 kb both upstream and downstream of the endogenous translational start site located in exon 2. The vector contained a cassette with an NLS-cre gene followed by an FRT-flanked neomycin resistance (neo) gene inserted just before the start site in exon 2 to drive cre expression from the endogenous DAT-promoter (FIG. 1A). The knockin locus was introduced into embryonic stem (ES) cells by homologous recombination. After passage through the germline we verified the presence of both the wild-type (wt) and the knockin (DAT-cre$^{neo}$) allele in the heterozygous mice (FIG. 1B).

The presence of the neo gene in this targeted locus could potentially lead to several problems. Neo contains a cryptic splice site which can cause abnormal splicing and thereby affect the normal expression of the DAT-locus. Furthermore, the expression of neo is driven by the thymidine kinase (tk) promoter which may recruit excess amounts of transcriptional elements to the locus, thereby causing ectopic expression of cre in non-DA cells. In our experimental strategy we circumvented this problem by flanking the neo gene with FRT-sites, enabling us to later remove neo by crossing the DAT-cre$^{neo}$ mice to FLPe deleter mice thus generating DAT-cre mice (FIG. 1A). We demonstrated the excision of neo both by Southern blot (FIG. 1B) and by PCR (FIG. 1C).

Expression Pattern of cre in Homozygous Knockout Mice

When DAT-cre$^{neo}$ and DAT-cre mice were crossed with mice homozygous for a loxP-flanked Tfam allele (Tfam$^{loxP}$/Tfam$^{loxP}$) we only observed unspecific recombination of the Tfam locus in tail DNA of DAT-cre$^{neo}$ mice but not in tail DNA of DAT-cre mice (FIG. 1C). When we repeated the Tfam genotyping using DNA from heart, kidney, liver, spleen, testis and cerebral cortex we again saw unspecific recombination of the Tfam allele in all tissues of DAT-cre$^{neo}$, mice but not in any tissue from DAT-cre mice (data not shown).

To study the cre expression in the brain we performed in situ hybridization on brain sections from DAT-cre mice using probes for both cre and tyrosine hydroxylase (TH), a commonly used marker for catecholamine neurons. The cre probe gave a clear hybridization signal in the ventral tegmental area (VTA) and in the substantia nigra pars compacta (SNpc), overlapping perfectly with the signal from the TH probe (FIG. 5A), thus demonstrating that the neurons expressing TH mRNA in the ventral mesencephalon (dopamine neurons) now co-expressed cre recombinase mRNA. To assess cre activity we also crossed DAT-cre mice with reporter mice that upon cre mediated excision of an upstream stop site express the lacZ gene from the ROSA26 locus (ROSA26-R). Fluorescence immunohistochemistry with β-gal antibodies showed a highly specific labeling confined to the DA neurons in the VTA and SNpc area very similar to the labeling achieved using TH antibodies (FIG. 5B). Thus, also at the protein level, there was a complete match between neurons expressing TH immunoreactivity and those expressing β-gal immunoreactivity.

Generation of Parkinson Mice

We wanted to generate mice with a parkinsonian phenotype by knocking out the gene for mitochondrial transcription factor A (Tfam) in dopaminergic neurons. Tfam has previously been knocked out in different tissues always resulting in slow and delayed cell death due to respiratory chain failure. To generate the Parkinson mice we used a two step breeding protocol. First DAT-cre mice were crossed to mice homozygous for a loxP-flanked Tfam allele (Tfam$^{loxP}$/Tfam$^{loxP}$). DA T-cre; +/Tfam$^{loxP}$ mice from this mating were identified and crossed again to Tfam$^{loxP}$/Tfam$^{loxP}$ mice. This cross generated the four possible genotypes in approximately Mendelian proportions (21%+/Tfam$^{loxP}$, 24% Tfam$^{loxP}$/Tfam$^{loxP}$, 27% DAT-cre; +/Tfam$^{loxP}$ and 29% DA T-cre; Tfam$^{loxP}$/Tfam$^{loxP}$).

DAT-cre; Tfam$^{loxP}$/Tfam$^{loxP}$ pups appeared normal, developed normally and gained weight as their littermates did (data not shown). At around 15 weeks of age they started to display PD-like symptoms such as abnormal gait and bradykinesia.

Decreased locomotion and reduced exploratory behaviour became apparent at that time. They still appeared to be relatively healthy though, with normal weight and a well groomed fur. This phenotype remained constant for several weeks with no further change in behavior or activity and no weight loss or other signs of decreased health status. We observed progression of symptoms with tremor, increased twitching and apparent limb rigidity at about 20 weeks of age. We provided the mice with moist food on the cage floor from about 20 weeks of age because motor impairment prevented them from reaching food and water normally provided on the grid covering the cage. However, even with this procedure, there was a slow gradual decline of weight as the neurodegeneration progressed (FIG. 2i), and the homozygous knockout mice had to be euthanized at about 45 weeks of age because of poor general condition.

Histochemistry of Knockout Brains

Next, we used histological analyses to characterize the neuropathology underlying the progressive deterioration of motor function in homozygous knockout mice (FIG. 3A-N). We performed TH immunofluorescence in newborn as well as 2 and 6 week old mice and found that the DA innervation of striatum appeared normal in homozygous knockout mice at these ages (FIG. 3A-C and data not shown). We first observed loss of DA nerve terminals in dorsolateral striatum at age 12 weeks and this loss progressed to involve most of the dorsal striatum as the homozygous knockout mice became older (FIG. 3C-F and data not shown). We also observed a subsequent reduction of DA nerve terminals in ventral striatum, from 20 weeks of age, which progressed to involve most areas of the ventral striatum (FIG. 3D-F). The striking end result was an almost complete loss of TH-immunoreactive nerve terminals (FIGS. 3M,N) in dorsal as well as ventral striatum, except for parts of nucleus accumbens, in 43 weeks old homozygous knockout mice (FIG. 3F).

Cresyl violet staining (not shown) and TH immunohistochemistry (FIG. 3I-L) revealed progressive loss of DA neurons in the homozygous knockout mouse midbrain. We observed DA nerve cell loss in SNpc, which predominantly innervates dorsal striatum, from age 12 weeks, whereas DA nerve cell loss in VTA, which predominantly innervates ventral striatum and cortical areas, was not obvious until 20 weeks of age in homozygous knockout mice (FIG. 3I-L). There was thus a very good correlation between the temporal and spatial progression of striatal DA denervation (FIG. 3C-F) and midbrain DA nerve cell loss (FIG. 3I-L).

Neurochemical studies with HPLC demonstrated a profound reduction of DA and its metabolites in striatum (caudate putamen and nucleus accumbens), SNpc, VTA and cortex in 20 weeks old homozygous knockout mice (FIG. 3O-Q). In dorsal striatum DA levels were reduced to about 1.5% of normal levels. We also found markedly increased ratios of homovallinic acid (HVA) and 3,4-dihydroxyphenylacetic acid (DOPAC) to DA, indicating an increased DA turnover in striatum of homozygous knockout mice at this age (FIG. 3Q). The loss of DA nerve cells and nerve terminals was thus accompanied by a corresponding loss of DA content in affected brain regions.

Many TH positive neurons of homozygous knockout mice contained rounded TH negative regions in their cytoplasm and we therefore performed confocal microscopy studies revealing that these areas were occupied by intracytoplasmic aggregates of α-synuclein-immunoreactivity (FIG. 4A-B). We detected small α-synuclein-immunoreactive aggregates in many DA neurons in SNpc and in a few DA neurons in VTA from 6 weeks of age in homozygous knockout mice. These α-synuclein aggregates became larger and more abundant as the homozygous knockout mice aged and were present in most remaining DA neurons of SNpc and VTA from 16 weeks of age onwards. No α-synuclein-immunoreactive inclusions were observed in A12 DA neurons of homozygous knockout mice (FIG. 4D) or in SNpc, VTA or A12 DA neurons of control mice at different ages (not shown).

DA neurons in patients with Parkinson's disease often have intracytoplasmic Lewy bodies, which contain ubiquitin-conjugated α-synuclein aggregates (Dauer et al., Neuron 39, 889-909 (2003)). We therefore performed additional confocal microscopy and found that the α-synuclein-immunoreactive aggregates were not immunoreactive for ubiquitin in younger homozygous knockout mice (not shown). However, a subset of the α-synuclein aggregates was also immunoreactive for ubiquitin in homozygous knockout mice older than 20 weeks (FIG. 4C).

TUNEL labeling did not reveal any DA neurons undergoing apoptotic death in mesencephalon of homozygous knockout mice at different ages (not shown). We also performed immunohistochemistry to detect glial fibrillary acidic protein (GFAP) and found no significantly increased expression in striatum and a very slight increase in SNpc (not shown) of homozygous knockout mice. These observations suggest that the cell death in SNpc and VTA of homozygous knockout mice is a continuous and slowly progressive process that is not associated with any marked astroglial response.

Behavioral Analysis of Parkinson Mice

We performed behavioral tests of homozygous knockout and control mice of different ages to obtain quantitative measurements of the clinically obvious motor impairment. We found a trend towards lower counts for both locomotion (FIG. 2A) and rearing (FIG. 2D) in 10 week old homozygous knockout mice, but these differences were not statistically significant. However, we found a clear reduction of both locomotion (FIG. 2B) and rearing (FIG. 2E) in 14 week old homozygous knockout mice and both of these activities declined progressively as homozygous knockout mice grew older (FIGS. 2C,F). We also induced motor activity with the Rota-Rod and found a trend towards decreased performance in 10 week old homozygous knockout mice (FIG. 2G) and a significant reduction in 14 week old homozygous knockout mice (FIG. 2H). Control mice typically improved their performance on the Rota-Rod as the test was repeated (FIGS. 2G,H). Most of the 14 week old control mice remained on the rod for the full 300 seconds of the experiment during the third trial, whereas homozygous knockout mice of the same age were unable to improve their locomotor performance (FIG. 2H). Strikingly, the homozygous knockout mice were unable to move for an extended period of time after that they had fallen off the Rota-Rod, whereas control mice immediately started to explore the new surroundings.

We used a standard Parkinson's disease drug containing L-DOPA (Madopark, Roche) to treat 20 and 30 week old homozygous knockout mice and observed improved motor performance (FIG. 4E-H). Interestingly, an identical L-DOPA dose elicited a more pronounced and longer lasting locomotion response in the younger homozygous knockout mice (FIGS. 4E,F), whereas the increase in rearing was similar in homozygous knockout mice at both ages (FIGS. 4G,H). The locomotor response abruptly terminated in the older homozygous knockout mice resembling the "wearing off" effect seen clinically.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof. Patent applications, patents and literature references cited herein indicate the knowledge in this field and are hereby incorporated by reference in their entirety. Where inconsistent interpretations are possible, the disclosure herein controls.

The invention claimed is:

1. A transgenic mouse genetically modified to have respiratory chain dysfunction in dopaminergic (DA) neurons only or genetically modified to lack respiratory chain function in DA neurons only, whose genome comprises a selectively suppressed or deleted mitochondrial transcription factor A (Tfam), and which develops pathophysiological features of Parkinson's disease selected from the group consisting of slow progressive loss of DA terminals in striatum and loss of DA neurons in SNpc; intracellular inclusions similar to Lewy bodies in affected areas prior to and during cell loss; and progressive movement disorder that is partially reversed by L-DOPA treatment, associated with abnormal gait, tremor and rigid limbs.

2. The transgenic mouse according to claim 1, wherein said mouse is genetically modified to lack oxidative phosphorylation function in dopaminergic (DA) neurons only, or to have oxidative phosphorylation dysfunction in DA neurons only.

3. A method for producing the transgenic mouse according to claim 1, comprising the steps of:
   a) providing a first group of mice, said first group of mice being homozygous for a loxP-flanked Tfam allele ($Tfam^{loxP}/Tfam^{loxP}$);
   b) providing a targeting vector comprising a cre gene inserted into a dopamine transporter locus;
   c) introducing said targeting vector into embryonic stem cells originating from said first group of mice to create recombinant embryonic stem cells by homologous recombination;
   d) growing said recombinant embryonic stem cells according to known methods thereby obtaining a transgenic mouse expressing said cre gene in dopaminergic (DA) neurons; and
   e) crossing said first group of mice being homozygous for a loxP-flanked Tfam allele ($Tfam^{loxP}/Tfam^{loxP}$) with said transgenic mouse expressing said cre gene in DA neurons, thereby obtaining the transgenic mouse of claim 1.

4. A method for investigating whether a chemical compound could be used for treating Parkinson's disease, comprising the steps of
   a) providing the transgenic mouse according to claim 1;
   b) providing a chemical compound to be tested;
   c) exposing said transgenic mouse to said compound to be tested; and
   d) investigating whether said chemical compound to be tested affects locomotion and/or rearing of the transgenic mouse, wherein an increase in locomotion and rearing of the transgenic mouse after exposure to said compound indicates that said compound could be used for treating Parkinson's disease.

5. The method of claim 3 wherein said cre gene is NLS-cre.

* * * * *

SEQUENCE LISTING

```
<160> NUMBER OF SEQ ID NOS: 12

<210> SEQ ID NO 1
<211> LENGTH: 48
<212> TYPE: DNA
<213> ORGANISM: Artificial
<220> FEATURE:
<223> OTHER INFORMATION: synthetic probe

<400> SEQUENCE: 1
caccagagac ggaaatccat cgctcgacca gtttagttac ccccagcc              48

<210> SEQ ID NO 2
<211> LENGTH: 20
<212> TYPE: DNA
<213> ORGANISM: Artificial
<220> FEATURE:
<223> OTHER INFORMATION: synthetic probe

<400> SEQUENCE: 2
agagacggaa atccatcgct                                            20

<210> SEQ ID NO 3
<211> LENGTH: 20
<212> TYPE: DNA
<213> ORGANISM: Artificial
<220> FEATURE:
<223> OTHER INFORMATION: synthetic probe

<400> SEQUENCE: 3
cccaacttga gatgtatgaa                                            20

<210> SEQ ID NO 4
<211> LENGTH: 19
<212> TYPE: DNA
<213> ORGANISM: Artificial
<220> FEATURE:
<223> OTHER INFORMATION: synthetic probe

<400> SEQUENCE: 4
caagaagcgc tttactgac                                             19

<210> SEQ ID NO 5
<211> LENGTH: 20
<212> TYPE: DNA
<213> ORGANISM: Artificial
<220> FEATURE:
<223> OTHER INFORMATION: synthetic probe

<400> SEQUENCE: 5
ctgccttcct ctagcccggg                                            20

<210> SEQ ID NO 6
<211> LENGTH: 20
<212> TYPE: DNA
<213> ORGANISM: Artificial
<220> FEATURE:
<223> OTHER INFORMATION: synthetic probe

<400> SEQUENCE: 6
gtaacagcag acaacttgtg                                            20
```

```
<210> SEQ ID NO 7
<211> LENGTH: 38
<212> TYPE: DNA
<213> ORGANISM: Artificial
<220> FEATURE:
<223> OTHER INFORMATION: synthetic probe

<400> SEQUENCE: 7
ggtgtgcagc tcatcctgga cccctccaa ggagcgct                         38

<210> SEQ ID NO 8
<211> LENGTH: 48
<212> TYPE: DNA
<213> ORGANISM: Artificial
<220> FEATURE:
<223> OTHER INFORMATION: synthetic probe

<400> SEQUENCE: 8
gcccggaccg acgatgaagc atgtttagct ggcccaaatg ttgctgga             48

<210> SEQ ID NO 9
<211> LENGTH: 20
<212> TYPE: DNA
<213> ORGANISM: Artificial
<220> FEATURE:
<223> OTHER INFORMATION: synthetic probe

<400> SEQUENCE: 9
cacgaccaag tgacagcaat                                            20

<210> SEQ ID NO 10
<211> LENGTH: 20
<212> TYPE: DNA
<213> ORGANISM: Artificial
<220> FEATURE:
<223> OTHER INFORMATION: synthetic probe

<400> SEQUENCE: 10
ctctgaagca catggtcaat                                            20

<210> SEQ ID NO 11
<211> LENGTH: 22
<212> TYPE: DNA
<213> ORGANISM: Artificial
<220> FEATURE:
<223> OTHER INFORMATION: synthetic probe

<400> SEQUENCE: 11
atgaaccagg tcttgagtct gg                                         22

<210> SEQ ID NO 12
<211> LENGTH: 22
<212> TYPE: DNA
<213> ORGANISM: Artificial
<220> FEATURE:
<223> OTHER INFORMATION: synthetic probe

<400> SEQUENCE: 12
cagggtcgga gagtcataca ac                                         22
```